Figure 1:
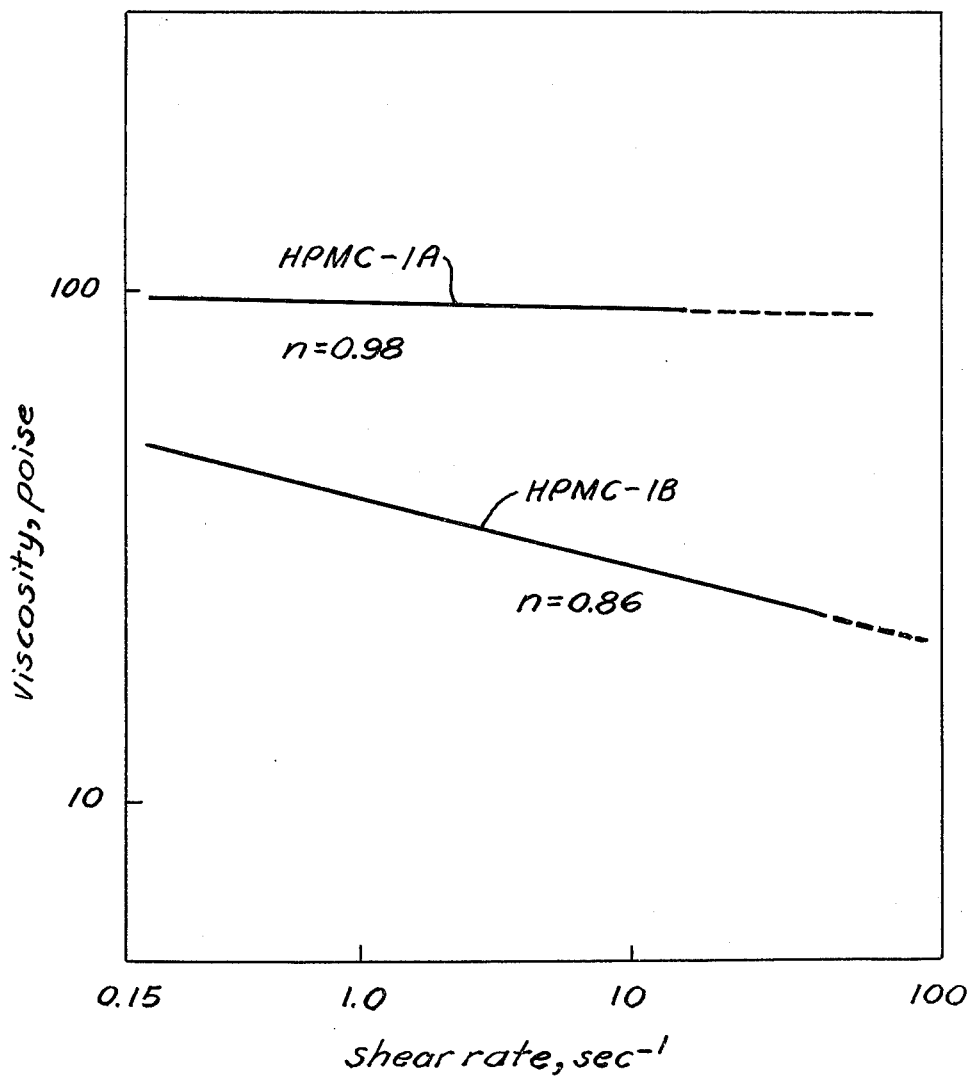

United States Patent [19]

Sarkar

[11] 4,001,211
[45] Jan. 4, 1977

[54] PHARMACEUTICAL CAPSULES FROM IMPROVED THERMOGELLING METHYL CELLULOSE ETHERS

[75] Inventor: Nitis Sarkar, Midland, Mich.
[73] Assignee: The Dow Chemical Company, Midland, Mich.
[22] Filed: Oct. 1, 1975
[21] Appl. No.: 618,549

Related U.S. Application Data

[63] Continuation-in-part of Ser. No. 528,830, Dec. 2, 1974, abandoned.
[52] U.S. Cl. .................... 536/84; 106/170; 106/197 R; 264/25; 264/301; 264/DIG. 37; 424/35
[51] Int. Cl.$^2$ ................ B29C 13/00; C08B 11/08; C08B 11/193
[58] Field of Search .................... 260/231 A, 231 R; 264/25, 301, DIG. 37; 424/35; 106/170, 197 R

[56] References Cited
UNITED STATES PATENTS

| | | | |
|---|---|---|---|
| 2,526,683 | 10/1950 | Murphy | 264/304 |
| 3,014,808 | 12/1961 | Nyberg | 106/197 R |
| 3,453,261 | 7/1969 | Scherff | 260/231 A |
| 3,493,407 | 2/1970 | Greminger et al. | 264/301 |
| 3,617,588 | 11/1971 | Langman | 264/301 |
| 3,712,886 | 1/1973 | Koyanagi et al. | 260/231 R |
| 3,852,421 | 12/1974 | Koyanagi et al. | 260/231 R |
| 3,870,702 | 3/1975 | Koyanagi et al. | 260/231 R |

*Primary Examiner*—Ronald W. Griffin
*Attorney, Agent, or Firm*—David B. Kellom

[57] ABSTRACT

Improved thermogelling methyl cellulose ether compositions for use in preparing pharmaceutical capsules by the pin dip coating process are prepared by blending the properties of water soluble methyl and $C_2$-$C_3$ hydroxyalkyl cellulose ethers to achieve an essentially Newtonian dip coating solution and a rapid high thermal gel yield strength. These properties require a cellulose ether with a relatively narrow molecular weight distribution. Blends of low viscosity methyl cellulose and hydroxypropylmethyl cellulose provide particularly suitable dip solution properties, gel yield strength, and capsule dissolution rates.

10 Claims, 2 Drawing Figures

PHARMACEUTICAL CAPSULES FROM IMPROVED THERMOGELLING METHYL CELLULOSE ETHERS

CROSS REFERENCE TO RELATED APPLICATIONS

This application is a continuation-in-part of U.S. application Ser. No. 528,830 filed Dec. 2, 1974, now abandoned.

BACKGROUND OF THE INVENTION

In 1950 Murphy U.S. Pat. No. 2,526,683 first described a process for preparing methyl cellulose medicinal capsules by a dip coating process using the apparatus described in U.S. Pat. No. 1,787,777 or similar dip coating apparatus. The process consists of dipping a capsule forming pin pre-heated to 40°–85° C into a cellulose ether solution kept at a temperature below the incipient gelation temperature (10°–30° C), withdrawing the pins at a predetermined withdrawal speed and then placing the pins in ovens kept at temperatures above the gelation temperature (45°–85° C), exposing the pins to a lower temperature first and then gradually to higher temperature until the film is dry. The dry capsule is then stripped, cut to size and the body and caps are fitted together.

The resulting methyl cellulose capsules had several advantages over conventional gelatin capsules including resistance to microorganisms and greater stability under extreme humidity conditions. However, these capsules failed to dissolve in the gastrointestinal fluid at body temperature in an acceptable time. Furthermore, the different rheological properties of the thermally gelling methyl cellulose made handling on the Colton machines designed for gelatin extremely difficult.

To overcome some of these problems, Greminger and Davis, U.S. Pat. No. 3,493,407, proposed the use of non-thermal gelling dip coating solutions of certain hydroxyalkylmethyl cellulose ethers in aqueous solvents. Langman, U.S. Pat. No. 3,617,588, describes the use of an induction heater to thermally gel cellulose ether dip coated pins after removal from the coating bath. However, these advances have not yet met the rigid requirements of commercial production.

STATEMENT OF THE INVENTION

The invention relates to medicinal capsules, particularly to capsules of thermal gelling cellulose ethers such as methyl cellulose and hydroxypropylmethyl cellulose. These cellulose ethers are soluble in cold water and insoluble in hot water. The viscosity of aqueous solutions decreases with the rise in temperature and then rapidly increases through a relatively narrow range of temperature with gel formation a few degrees above the temperature at which minimum viscosity is observed.

This thermogelling characteristic is critical to the dip coating process. However, some rigid restrictions that the solution must follow from a rheological standpoint have now been identified by further research. These discoveries have led to improved methyl cellulose ether compositions for producing medicinal capsules. By controlling the non-Newtonian properties of cellulose ether solution, the gel strength at elevated temperature, and the solution rate of the capsules by proper adjustment of the cellulose ether molecular weight, MW distribution, degree and type of substitution, improved medicinal capsules are obtained.

More specifically, these improved cellulose ether compositions for use in preparing pharmaceutical capsules by the pin dip coating process are characterized by having:

A. A methoxyl degree of substitution (DS) of about 1.5–2.0 and a $C_2$–$C_3$ hydroxyalkoxyl molar substitution (MS) of about 0.1–0.4;

B. As a 2 wt % aqueous solution, a viscosity of about 2–10 cps at 20° C and a thermal gel point of about 50°–80° C;

C. As a 15–30 wt % aqueous solution at 20° C, a viscosity of about 1,000–10,000 cps with essentially Newtonian fluid properties as defined by a power law coefficient, $n$, of 0.9–1.0 at shear rates of between 0.1–10 $sec^{-1}$; and D. As a 15–30 wt % aqueous solution, a 50 sec gel yield strength at 65° C of at least 150 dynes/$cm^2$.

In practice the capsules are prepared by dipping pins preheated to about 40°–85° C in an aqueous dip coating bath containing about 15–30 weight percent of the improved cellulose ether composition at a bath temperature below about 40° C. The dip coated pins are then withdrawn and dried at a temperature above the gel point of the cellulose ether to obtain the dry capsule shells.

General Description — Rheological Requirements

In spite of continued developments in the design of capsule dip baths, as shown for example by Whitecar, U.S. Pat. No. 3,592,445, the rheological requirements of the dip solution used with the Colton capsule machines have not been previously examined in detail.

When the hot pin is dipped into the solution in the dipping dish, the solution gels in the surface of the pin and as the pin is withdrawn, a film of gelled liquid of certain thickness is formed on the pin. The pin is then turned 180° to an upright position and placed in the oven to dry. To obtain the desired 4±0.5 mils dry film thickness, a wet gel thickness of about 20–60 mils is required. Furthermore it is essential that the wet gel film thickness as the pin is withdrawn be quite uniform and that the wet film have sufficient strength to prevent rundown or other distortion from gravitational pull on the film or rotational forces as the pin moves to the drying oven.

To achieve the essential uniform coating of the pins with a wet thermal gel of sufficient strength, requires that the cellulose ether dip coating solution and the thermal gel meet some rigid rheological requirements.

First the cellulose ether concentration of the solution in the dipping dish must be sufficiently high (15–30 percent) to ensure proper film formation and ease of drying. Then the complex flow patterns in the dipping dish and around the pins result in a shear rate on the moving pin that varies from point to point. To obtain uniform wet gel film thickness under these conditions requires that the dipping solution be essentially Newtonian.

Assuming a 12.5 percent variation of film thickness is acceptable (4.0±0.5 mils), the viscosity variation between the highest and lowest shear rates on the pin should not be more than 25 percent. Using the standard viscosity power-law equation (cf. Van Wazer ea "Viscosity and Flow Measurement", Interscience Publishers, New York, 1963, p. 15):

$$\eta = K\sigma^{n-1}$$

where $\eta$ is the viscosity, $\sigma$ the shear rate, $K$ the consistency index constant, and $n$ the power law coefficient, it has been found essential that the dip coating solution have a power law coefficient of 0.9–1.0 over a shear rate range of 0.1–10 sec$^{-1}$ to achieve the requisite gel film uniformity.

Such an essentially Newtonian solution ($n$=0.9–1.0), can be obtained by appropriate control of the cellulose ether molecular weight and dip bath conditions. Thus as shown further in the examples it is important to keep:

1. The molecular weight fairly low, i.e., a 2 wt % aqueous solution viscosity of about 2–10 cps at 20° C;
2. The molecular weight distribution fairly low with minimum amount of very high MW fractions, i.e., less than about 0.1 wt % MW above 200,000;
3. The salt concentration in the bath less than 1 wt % and
4. The dip bath concentration and temperature as low as possible consistent with the necessary wet gel thickness.

The importance of the molecular weight distribution is shown in FIG. 1. The two hydroxypropylmethyl cellulose ether samples have essentially the same chemical composition and 2 percent aqueous solution viscosities. However Sample B, with a wide molecular weight distribution and more than 0.15 weight percent of a very high MW fraction, has a wholly unacceptable power law coefficient of 0.86. In general a $M_w/M_n$ ratio less than about 3.5 is desired.

Secondly, in order to prevent rundown or other displacement of the wet thermal gel film prior to oven drying, the gel must have enough yield strength to counteract gravitational and rotational stresses while in wet form on the pin. For normal Size 000 to Size 5 pharmaceutical capsule body and cap pins (average diameters of 0.452–0.983 cm), yield values (S) calculated as a function of wet gel thickness required to eliminate rundown of wet gel range from about 60 to 160 dynes/cm$^2$ for wet film thicknesses of 20–50 mils. In practice a wet gel yield strength of at least 150 dynes/cm$^2$ measured after 30–50 sec at 65° C is desirable to cover the normal range of capsule sizes.

Factors found to influence the wet gel strength of aqueous cellulose ether solutions include:

1. The degree and type of alkyl substitution;
2. A high cellulose ether molecular weight;
3. High cellulose ether concentrations; and
4. High pin and oven temperatures.

Clearly a proper balance must be achieved of properties affecting the Newtonian character of the dip bath and the strength of the wet gel.

Methyl Cellulose Ethers

Critical to this invention are certain properties of the thermogelling methyl cellulose ether composition. That it has a 2 percent aqueous solution viscosity of about 3–10 cps and gel point of about 50°–80° C was recognized in the prior art. Also the degree and type of ether substituents is known to affect the rate of capsule dissolution in gastrointestinal fluid. However, the criticality of the molecular weight distribution, the wet gel yield strength, and the effect of the substituents on the gel strength have not been previously identified.

Required is a methyl cellulose ether composition having a methoxyl DS of about 1.5–2.0 and a $C_2$-$C_3$ hydroxylalkoxyl MS of about 0.1–0.4. The substituents can be combined in a single hydroxyalkylmethyl cellulose ether such as a hydroxypropylmethyl cellulose ether having a methoxyl DS of about 1.50–2.00 and a hydroxypropoxyl MS of about 0.1–0.3 and a 2 percent aqueous solution viscosity of about 2–10 cps at 20° C.

Alternately compositions with suitable substitution can be obtained by blending methyl cellulose with non-ionic hydroxyalkyl cellulose ethers. Particularly useful are blends of a methyl cellulose having a methoxyl DS of about 1.64–1.90 and a 2 percent aqueous solution viscosity at 20° C of about 5–4000 cps with hydroxypropylmethyl cellulose hydroxyethylmethyl cellulose, hydroxypropyl cellulose, hydroxyethyl cellulose, hydroxyethylhydroxypropylmethyl cellulose, etc. Most useful are non-ionic hydroxyalkyl cellulose ethers having a 2 percent aqueous solution viscosity of about 2–10 cps at 20° C. and a thermal gel point below 100° C. Thus as shown in Example 2B blends of 20–50 weight percent methyl cellulose (methoxyl DS of 1.64–1.90) and 80–50 weight percent hydroxypropylmethyl cellulose (methoxyl DS of 1.68–1.80, hydroxypropoxyl MS of 0.17–0.30) provide a ready means for controlling rheological and other properties critical to this invention.

For example, a capsule prepared from 9 cps methyl cellulose (1.64–1.90 DS) required 20 minutes to dissolve under normal gastrointestinal conditions in contrast to the usual 3 minutes for gelatin capsules. But a 1:2.67 blend of this methyl cellulose with 2–10 cps hydroxypropylmethyl cellulose provides a capsule that dissolves in 4 minutes.

Suitable cellulose ethers are commercially available. However, their normal characterization by viscosity and type and degree of substitution is not alone adequate to define the improved cellulose ether compositions. As shown in Example 1, the rheological characteristics of the aqueous dip bath are extremely sensitive to other properties of the cellulose ether. To obtain an essentially Newtonian solution as defined by a power law coefficient ($n$) of 0.9–1.0 at shear rates of between 0.1–10 sec$^{-1}$ requires a fairly narrow molecular weight range and elimination of any very high MW fractions. The presence of as little as 0.1 weight percent of a cellulose ether fraction having a molecular weight above about 200,000 will cause the solution to be non-Newtonian ($n$<0.9).

In practice, the power law coefficient determined at dip bath concentration (15–30 weight percent) and temperature (below about 40° C) at shear rates between 0.1–10 sec$^{-1}$ is an accurate and functional measure of a suitable cellulose ether composition.

The gel strength of the cellulose ether solution is also greatly influenced by the ether substituents. Firmest gels are obtained with methyl substitution while hydroxyalkyl substituents provide softer gels with usually higher gel point temperatures. As noted above, a 50 sec yield value of at least 150 dynes/cm$^2$ and preferably about 150–300 dynes/cm$^2$ is required for effective operation with normal size capsule pins.

Again a direct measurement of the wet gel strength provides suitable process control. Also blends provide a ready means for adjustment to achieve the desired final properties.

Finally, note that the solution rate and gel strength both depend on hydroxypropyl substitution but in an opposite way. That is, solution rate of cellulose ether films increases and gel strength decreases with increasing hydroxypropyl substitution. So, a compromise has to be made to obtain a suitable solution rate and yield stress. This can be achieved by optimizing MS of hydroxyalkyl substitution and blending methyl cellulose with hydroxypropylmethyl cellulose.

Dip Coating Process

In practice, the improved pharmaceutical capsules are obtained by dipping capsule pins preheated to about 40°–85° C in an aqueous dip coating bath containing about 15–30 weight percent of the methyl cellulose compositions defined above. The dip coating bath is held at an operational temperature below about 40° C, and usually between about 10°–30° C. An operational viscosity of about 1000–10,000 cps, and preferably about 2000–5000 cps is desirable.

As the preheated pins dip into the coating bath, the cellulose ether thermally gels on the surface of the pin. When the pins are withdrawn, a film of gelled cellulose ether remains on the pin. A wet thermal gel film thickness of about 20–60 mils, preferably about 30–50 mils, is necessary to obtain a final dry film thickness of 4±0.5 mils. The coated pins then travel through an oven held at temperatures above the cellulose ether gelation temperature. The dry capsule pieces are then stripped, cut to size, and fitted together.

Normally, the cellulose ether capsules are relatively clear and transparent. However, if opaque capsules are desired, a minor amount of inert non-toxic pigment such as powdered charcoal or finely divided titanium dioxide can be incorporated in the coating composition. Conventional non-toxic dyes and fillers can also be used. For increased flexibility, an appropriate plasticizer such as glycerine, propylene glycol, or hydroxypropyl glycerine can be included in a moderate amount, e.g. 5 to 20 percent.

This process is particularly suited for preparing pharmaceutical capsule shells which dissolve at a rate comparable to gelatin capsules. Delay release characteristics can be obtained by incorporation of a less water-soluble cellulose ether such as ethyl cellulose as described by Greminger and Windover U.S. Pat. No. 2,887,440.

To illustrate further the present invention, the following examples are given. Unless otherwise specified, all parts and percentages are by weight. Solution viscosities are determined by the method of ASTM D-1347-64.

EXAMPLE 1

Dip Coating Bath Rheology

A. An aqueous dip coating solution containing 28.7 wt % of 3.96 cps (2 wt %, 20° C) hydroxypropylmethyl cellulose was prepared from a commercial methyl cellulose having a methoxyl DS of 1.68–1.80, a hydroxypropoxyl MS of 0.17–0.30 and a thermal gel point of about 60° C (Methocel 60HG from the Dow Chemical Company). Its viscosity at 30° C at shear rates of from about 0.1–10sec$^{-1}$ was determined using a Haake Rotovisco viscometer. The results are given in FIG. 1, Curve A. The power law coefficient ($n$) was 0.98 indicating an essentially Newtonian fluid under conditions suitable for capsule dip coating operation.

A portion of the dip coating solution was thermally gelled by heating in a water bath to about 50°–60° C. The yield value of the soft gel was determined using the Haake instrument and the on-off technique described by Van Wazer ea "Viscosity and Flow Measurement" op. cit., p. 79–80. Because of gel breakdown from the moving rotor, these measured yield values are lower than static values measured by the penetrometer method of A. J. Haighton, J. Am. Oil Chem. Soc., 36, 345(1959).

Further study of the Van Wazer method led to a more refined and accurate measure of the essentially instantaneous gel strength required for commercial dip coating operations. For this measurement, the rotor and bob of a Haake MV II rotoviscometer are preheated to 65° C, a 15–30 wt % aqueous solution of the cellulose ether is added, allowed to warm up and equilibrate for 30 seconds, and then the gel strength measured within a total time of 50 seconds. The resulting "50 sec" yield strength correlates well with the requirements of commercial capsule dip coating machines.

B. A second sample of hydroxypropylmethyl cellulose having similar methyl and hydroxypropyl substitution and a 2 wt % aqueous solution viscosity of 3.74 cps at 20° C was dissolved in water to give a 27.0 wt % solution. Its viscosity was also measured at 30° C over a similar range of shear rates with the results given in FIG. 1, Curve B. The calculated power law coefficient was 0.86 suggesting a different molecular weight distribution of the two cellulose ethers.

Figure 2:
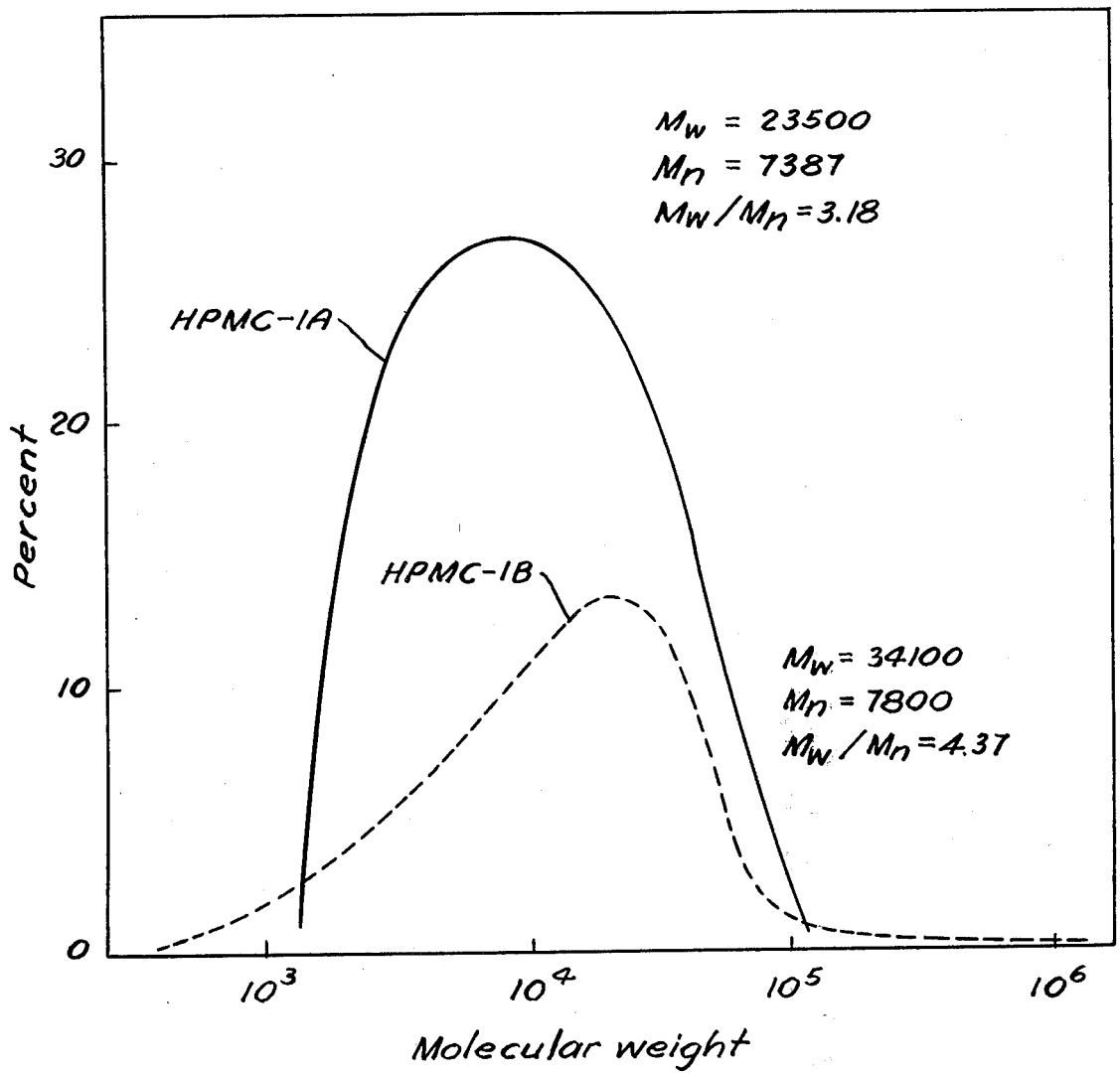

C. The different molecular weight distributions for the two cellulose ethers, HPMC 1A and 1B, was confirmed by gel permeation chromatography as shown in FIG. 2.

D. When examined in a laboratory dip test with Size O pins, Solution 1A gave essential uniformly coated pins while Solution 1B gave stringy tails and visible non-uniformity when withdrawn from the dip bath. However, neither solution had sufficient gel strength to prevent subsequent run down and formation of tires, striations and other defects during drying.

EXAMPLE 2

Wet Thermal Gel Strength

When a preheated pin is dipped into the aqueous cellulose ether dip coating bath, a portion of the solution gels on the pin to form a wet gel coating which clings to the pin as it is withdrawn. To prevent run down and loss of the essentially uniform coating required for mating capsule shells, the gel must have sufficient yield strength to maintain its form as it moves from the dip bath to the drying oven.

A. The wet thermal gel strength of the methyl cellulose ether compositions can be determined as described in Example 1A. Using standard equations, known dimensions for capsule body and cap pins, and desired final capsule film thickness of 4±0.5 mils, a table of yield values has been calculated for each pin size and wet gel thickness of 20–60 mils. Typical calculated values for 35 and 50 mil wet films are given in Table 2.

Table 2

| Pin Size | Av. Dia cm | Calculated Yield Values (S) to Eliminate Rundown Yield Value, dynes/cm$^2$ | |
|---|---|---|---|
| | | 35 mils | 50 mils |
| 000 | 0.940 | 95.4 | 141.3 |
| 0 | 0.716 | 98.0 | 146.5 |
| 2 | 0.592 | 100.0 | 151.2 |
| 5 | 0.452 | 104.3 | 159.4 |

B. Once the significance of the wet gel yield strength to the capsule dip coating process has been recognized, it provides a simple and effective test for evaluating methyl cellulose compositions for use in this process.

Table 3 provides a simple illustration of the effect of blending methyl cellulose (MC) with a hydroxypropylmethyl cellulose (HPMC) to improve its yield value or wet gel strength. The methyl cellulose (MC-2B) had a methoxyl DS of 1.64–1.90 and a 2 wt % aqueous solution viscosity of 11 cps at 20° C. The hydroxypropylmethyl cellulose (HPMC-2B) had a methoxyl DS of 1.68–1.80, a hydroxypropyl MS of 0.17–0.30, and a viscosity of 3.75 cps (2 wt %, 20° C.) The test solutions contained a total of 22 wt % cellulose ether and were gelled by heating at 55°–60° C.

Table 3

| Yield Values of Blended HPMC and MC | | | | |
|---|---|---|---|---|
| Conc. HPMC | Wt% MC | Ratio HPMC/MC | 20% Visc. cps, 20° C | 50 Sec Yield* dynes/cm$^2$ |
| 22 | 0 | — | 2285 | 102 |
| 20 | 2 | 10 | 3415 | 142 |
| 19 | 3 | 6.67 | 4198 | 175 |
| 18 | 4 | 4.5 | 5221 | 205 |
| 17 | 5 | 3.4 | 6429 | 245 |
| 16 | 6 | 2.67 | 7864 | 286 |

*Modified Van Wazer method, 65° C

EXAMPLE 3

Capsules from HPMC-MC Blends

A. An aqueous dip coating solution was prepared by dissolving a blend of 72.7 parts of 3.75 cps hydroxypropylmethyl cellulose (Methocel 60 HG, 1.8 methoxyl DS, 0.30 hydroxypropoxyl MS, 2 percent gel point of 60° C.)

27.3 parts of 11.0 cps methyl cellulose (Methocel MC, 1.80 methoxyl DS, 2 percent gel point of 50° C.)

in sufficient water to give a solution containing 22.0 weight percent cellulose ether. The solution had a viscosity of about 5000 cps at 30° C and was essentially Newtonian at shear rates from 0.1–10 sec$^{-1}$ with a power law coefficient ($n$) of 0.95. Its gel point was about 35° C. A firm rigid gel was obtained at 50° C with a yield value of about 101 dynes/cm$^2$ as measured by the Van Wazer method.

B. Capsule shells were prepared from this HPMC-MC dip solution using No. O capsule pins machined from Type 313 stainless steel and lightly coated with a lubricant using a standard Colton dip coating machine. Pins preheated to about 65° C were dipped into the HPMC-MC solution held at 30° C and after 10–15 sec smoothly withdrawn, inverted, and passed through the oven drier held at 50°–70° C. The resulting capsule shells were stripped from the pins and examined for uniformity and dissolution time. In clarity, freedom from surface defects, uniformity, ease of assembling cap and body shells, these HPMC-MC shells met the standard set for pharmaceutical capsules. The average dissolution time was 4 minutes.

C. Table 4 presents data from blends of methyl cellulose and other hydroxypropyl cellulose ethers.

Table 4

| Cellulose Ethers[1] | | Ratio | Other MC Blends Aq. Soln, 20° C | | 50 Sec Yield, 65° C dynes/cm$^2$ |
|---|---|---|---|---|---|
| | | | Wt% CE | Visc. cps | |
| 4–1 | HPMC-3/MC-2 | 20/2 | 22 | 5334 | 245 |
| | | 19/3 | 22 | 7552 | 296 |
| 4–2 | HPMC-3/MC-3 | 18/4 | 22 | 8811 | 259 |
| 4–3 | HPMC-3/MC-4 | 17.5/4.5 | 22 | 9871 | 297 |
| 4–4 | HPMC-4/MC-2 | 16/2 | 18 | 2718 | 146 |
| | | 15/3 | 18 | 4189 | 185 |
| 4–5 | HPC-1/MC-2 | 14/3 | 17 | 3259 | 50* |
| | | 10/5 | 15 | 7368 | 120* |
| 4–6 | HPC-1/MC-1 | 8/8 | 16 | 4204 | 185 |
| | | 7/9 | 16 | 4690 | 220 |
| | | 5/10 | 15 | 5140 | 265 |

[1]HPC-1  3,4 cps hydroxypropyl cellulose (2.5–4 MS)
HPMC-3  3,6 cps hydroxypropylmethyl cellulose (1.88 DS; 0.21 MS)
HPMC-4  3,7 cps hydroxypropylmethyl cellulose (1.38 DS; 0.20 MS)
MC-2  25 cps methyl cellulose (1.83 DS)
MC-3  16 cps methyl cellulose (1.83 DS)
MC-4  14 cps methyl cellulose (1.83 DS)
MC-1  11 cps methyl cellulose (1.80 DS)
*Unsatisfactory for capsule process D. In a similar manner capsules can be made from other thermogelling, blends of methyl cellulose and other non-ionic hydroxyethyl and hydroxypropyl cellulose ethers which provide an essentially Newtonian dip bath solution and a thermal gel of requisite yield strength to provide a dimensionally uniform and stable wet gel coating.

EXAMPLE 4

Capsules from Other Cellulose Ethers

Table 5 gives typical 50 second yield values for a number of other low viscosity cellulose ethers.

Table 5

| Cellulose Ether[1] | | 50 Second Yield Values, 65° C | | | | |
|---|---|---|---|---|---|---|
| | | Composition, Wt % | | Aq. Soln 20° C | | 50 Sec Yield |
| | | MeO(DS) | HAO(MS) | Wt % CE | Visc | dynes/cm$^2$ |
| 5–1 | 3.66 cps EHEC | −35 wt % | ethoxyl- | 20 | 10280 | 255 |
| 5–2 | 3.33 cps HEMC | 1.37 | 0.38 | 18 | 1277 | 162 |
| 5–3 | 3.37 cps HEMC | 1.55 | 0.21 | 18 | 1262 | 168 |
| 5–4 | 3.43 cps HBMC | 1.41 | 0.08 | 18 | 1598 | 168 |
| 5–5 | 3.77 cps HBMC | 1.27 | 0.13 | 18 | 3079 | 198 |
| 5–6 | 4.03 cps HBMC | 1.46 | 0.19 | 20 | 6318 | 272 |
| 5–7 | 2.76 cps HPMC | 1.79 | 0.03 | 18 | 811 | 193 |

Table 5-continued

| Cellulose Ether[1] | | 50 Second Yield Values, 65° C Composition, Wt % | | Aq. Soln 20° C | | 50 Sec Yield dynes/cm$^2$ |
|---|---|---|---|---|---|---|
| | | MeO(DS) | HAO(MS) | Wt % CE | Visc | |
| 5-8 | 2.77 cps HPMC | 1.77 | 0.10 | 25 | 3278 | 270 |
| 5-9 | 2.88 cps HPMC | 1.72 | 0.12 | 25 | 3239 | 190 |
| 5-10 | 2.90 cps HPMC | 1.69 | 0.17 | 25 | 2494 | 160 |

[1]EHEC - Ethylhydroxyethyl cellulose
HEMC - Hydroxyethylmethyl cellulose
HBMC - Hydroxybutylmethyl cellulose
HPMC - Hydroxypropylmethyl cellulose Such data, coupled with the Newtonian properties of the aqueous cellulose ether at dip bath operating conditions, provide requisite rheological information for capsule dip coating operations.

I claim:

1. A thermal gelling methyl cellulose ether composition suitable for use in preparing pharmaceutical capsules by an aqueous dip coating process using preheated pins and having a methoxyl DS of about 1.5-2.0, a $C_2$-$C_3$ hydroxyalkyl MS of about 0.1-0.4, a 2 wt. % aqueous solution viscosity of about 2-10 cps at 20° C and a thermal gel point of about 50°-80° C, and a 15-30 wt. % aqueous solution viscosity of about 1,000-10,000 cps at 20° C, said composition being further characterized by having as a 15-30 wt. % aqueous solution:
  A. Essentially Newtonian fluid properties as defined by a power law coefficient, $n$, of 0.9-1.0 at shear rates of between 0.1-10 sec$^{-1}$, and
  B. A 50 sec gel yield strength of at least 150 dynes/cm$^2$ at 65° C.

2. The cellulose ether composition of claim 1 where the cellulose ether is a blend of a methyl cellulose having a methoxyl DS of about 1.64-1.90 and a non-ionic $C_2$-$C_3$ hydroxyalkyl cellulose ether.

3. The cellulose ether composition of claim 2 where the non-ionic hydroxyalkyl cellulose ether has a thermal gel point of about 50°-90° C as a 2 percent aqueous solution.

4. The cellulose ether composition of claim 2 where the non-ionic cellulose ether is a hydroxypropylmethyl cellulose ether with a 2 percent aqueous solution viscosity of about 2-10 cps at 20° C.

5. The cellulose ether composition of claim 2 where the cellulose ether is a blend of (1) about 20-50 weight percent of methyl cellulose having a methoxyl DS of about 1.64-1.90 and (2) about 80-50 weight percent of a hydroxypropylmethyl cellulose having a methoxyl DS of about 1.68-1.80 and a hydroxypropoxyl MS of about 0.17-0.30.

6. The cellulose ether composition of claim 1 where the cellulose ether is a hydroxypropylmethyl cellulose ether with a methoxyl DS of about 1.50-2.00, a hydroxypropoxyl MS of about 0.1-0.3, and a 2 percent aqueous solution viscosity of about 2-10 cps at 20° C.

7. The cellulose ether composition of claim 1 where the cellulose ether has a narrow molecular weight distribution with a $M_w/M_n$ ratio less than about 3.5 and contains less than 0.1 wt % of material having a molecular weight above about 200,000.

8. In a process for preparing pharmaceutical capsules by an aqueous dip coating process using preheated pins and an aqueous bath containing about 15-30 wt. % of a thermal gelling methyl cellulose ether composition having a methoxyl DS of about 1.5-2.0, a $C_2$-$C_3$ hydroxyalkoxyl MS of about 0.1-0.4, a 2 wt. % aqueous solution viscosity of about 2-10 cps at 20° C and thermal gel point of about 50°-80° C, and a 15-30 wt. % aqueous solution viscosity of about 1,000-10,000 cps at 20° C, the improvement comprising using a methyl cellulose ether composition further characterized by having as a 15-30 wt. % aqueous solution:
  A. Essentially Newtonian fluid properties as defined by a power law coefficient, $n$, of 0.9-1.0 at shear rates of between 0.1-10 sec$^{-1}$, and
  B. A 50 sec gel yield strength of at least 150 dynes/cm$^2$ at 65° C, as the shell forming component of the aqueous dip coating bath.

9. The process of claim 8 where the cellulose ether has a 50 sec gel yield strength of 150-300 dynes/cm$^2$ at 65° C.

10. The process of claim 8 where size No. 1 capsule pins preheated to about 50°-60° C are dipped into a 20-30 wt % aqueous solution of a blend of (1) about 73 wt % of a hydroxypropylmethyl cellulose having a methoxyl DS of about 1.68-1.80 and a hydroxypropoxyl MS of about 0.17-0.30 and (2) about 27 wt % of methyl cellulose having a methoxyl DS of about 1.64-1.90 and the resulting dip coated pins are oven dried at about 45°-80° C to give capsule shells having a wall thickness of about 4±0.5 mils.

* * * * *